(12) United States Patent
Ng

(10) Patent No.: US 7,517,323 B2
(45) Date of Patent: Apr. 14, 2009

(54) ROTARY DEVICE TO GATHER MUCOUS FOR TESTING

(76) Inventor: Raymond C. Ng, Suite 1102, Hing Wai Bldg., 36 Queen's Road, Central (HK)

( * ) Notice: Subject to any disclaimer, the term of this patent is extended or adjusted under 35 U.S.C. 154(b) by 0 days.

(21) Appl. No.: 11/582,921

(22) Filed: Oct. 19, 2006

(65) Prior Publication Data

US 2007/0270715 A1  Nov. 22, 2007

Related U.S. Application Data

(63) Continuation-in-part of application No. 11/436,853, filed on May 19, 2006.

(51) Int. Cl.
*A61B 10/00* (2006.01)
(52) U.S. Cl. .................................................. 600/569
(58) Field of Classification Search ................. 600/569
See application file for complete search history.

(56) References Cited

U.S. PATENT DOCUMENTS

| | | | |
|---|---|---|---|
| 2,955,592 A | 10/1960 | MacLean | |
| 3,554,185 A | 1/1971 | Kohl | |
| 3,626,470 A | 12/1971 | Antonides et al. | |
| RE27,915 E | 2/1974 | Kohl | |
| 3,796,211 A | 3/1974 | Kohl | |
| 3,881,464 A | 5/1975 | Levene | |
| 4,108,162 A * | 8/1978 | Chikashige et al. | 600/569 |
| 4,235,245 A * | 11/1980 | Naito | 600/569 |
| 4,493,125 A * | 1/1985 | Collis | 15/167.2 |
| 4,700,713 A * | 10/1987 | Kist | 600/569 |
| 4,754,764 A | 7/1988 | Bayne | |
| 4,759,376 A * | 7/1988 | Stormby | 600/569 |
| 4,936,312 A * | 6/1990 | Tsukagoshi | 600/562 |
| 5,062,730 A * | 11/1991 | Tomii et al. | 403/57 |
| 5,370,128 A * | 12/1994 | Wainwright | 600/569 |
| 5,713,369 A * | 2/1998 | Tao et al. | 600/569 |
| 5,795,309 A * | 8/1998 | Leet et al. | 600/569 |
| 5,899,850 A * | 5/1999 | Ouchi | 600/104 |
| 6,036,658 A * | 3/2000 | Leet et al. | 600/569 |
| 6,093,155 A * | 7/2000 | Ouchi | 600/569 |
| 6,101,659 A * | 8/2000 | Halm | 15/167.1 |
| 6,193,674 B1 * | 2/2001 | Zwart | 600/569 |
| 6,346,086 B1 * | 2/2002 | Maksem et al. | 600/569 |
| 6,352,513 B1 | 3/2002 | Anderson et al. | |
| D552,238 S * | 10/2007 | Zwart | D24/146 |
| 2001/0035191 A1 * | 11/2001 | Lee | 132/160 |

(Continued)

FOREIGN PATENT DOCUMENTS

WO    WO 9116855 A1 * 11/1991

*Primary Examiner*—Max Hindenburg
*Assistant Examiner*—Michael C. Stout
(74) *Attorney, Agent, or Firm*—William W. Haefliger

(57) ABSTRACT

A mucous gathering device, comprising an elongated rotatable stem having a longitudinal axis, and a rotary headpiece carried at an end of the stem for angular flexing as the stem rotates, the headpiece having a face sized for presentation to the cervix entrance as the head rotates about an axis angled relative to the stem, the face having associated flexible means for gathering and retaining mucous proximate the cervix as the headpiece rotates, and a flexible rotary probe carried by the headpiece, the probe projecting forwardly and centrally relative to associated means and defining edges spaced apart to gather and propel mucous toward the headpiece in response to probe rotation in an opening defined by the cervix.

13 Claims, 3 Drawing Sheets

U.S. PATENT DOCUMENTS

| | | | |
|---|---|---|---|
| 2002/0068881 A1* | 6/2002 | Kobren et al. | 600/569 |
| 2004/0083567 A1* | 5/2004 | Lies | 15/28 |
| 2004/0181170 A1* | 9/2004 | Wallach | 600/569 |
| 2005/0273961 A1* | 12/2005 | Moskovich et al. | 15/167.1 |
| 2005/0277847 A1 | 12/2005 | Belinson | |
| 2007/0073186 A1* | 3/2007 | Decker et al. | 600/569 |
| 2007/0093727 A1* | 4/2007 | Feuer et al. | 600/564 |

* cited by examiner

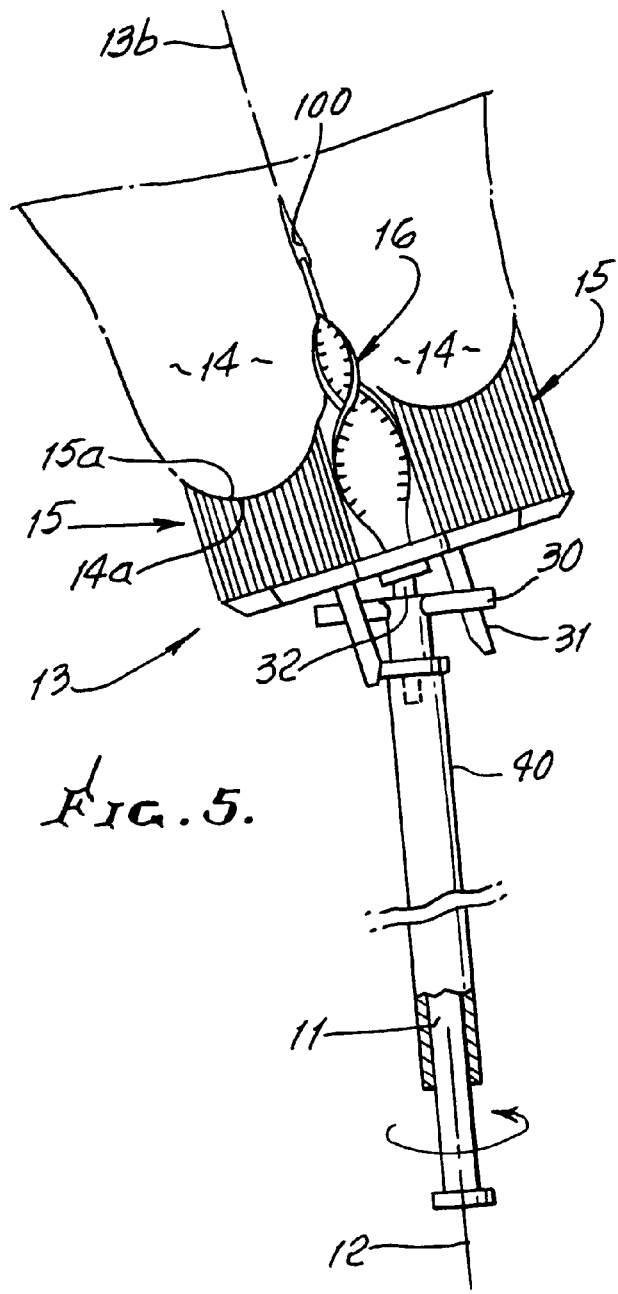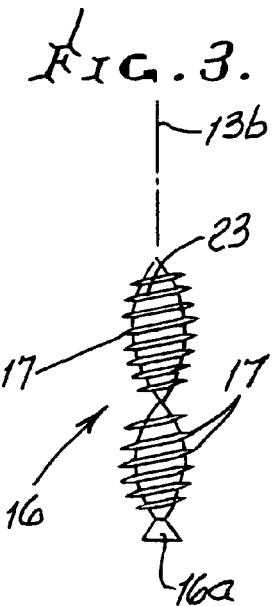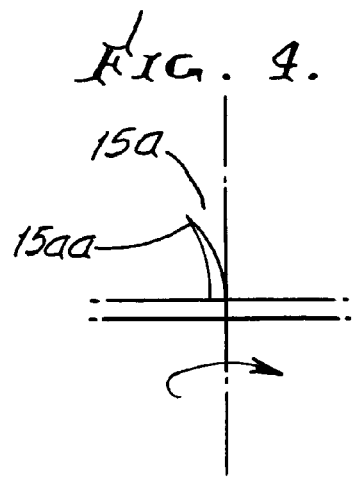

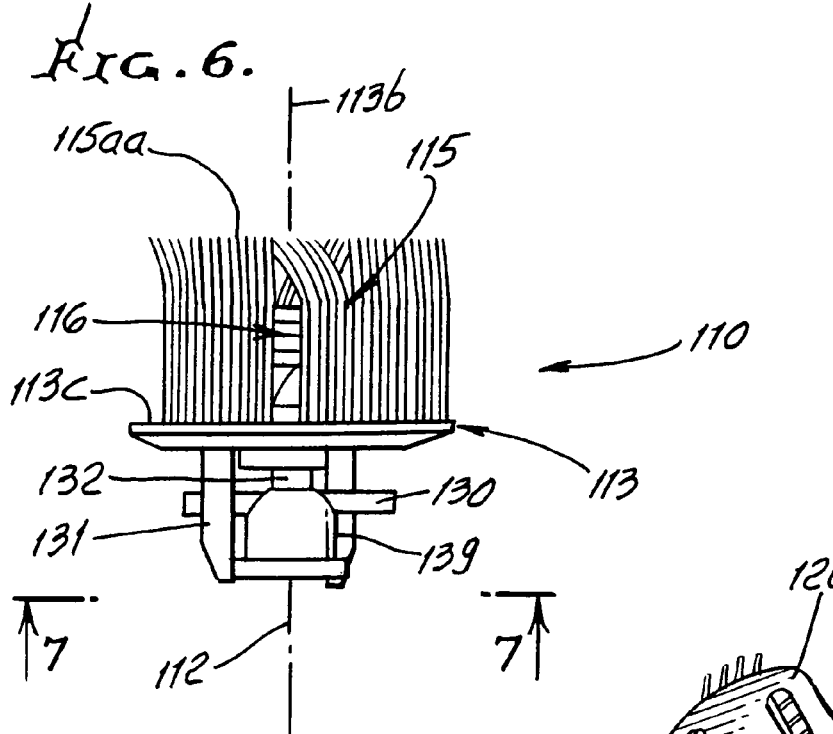
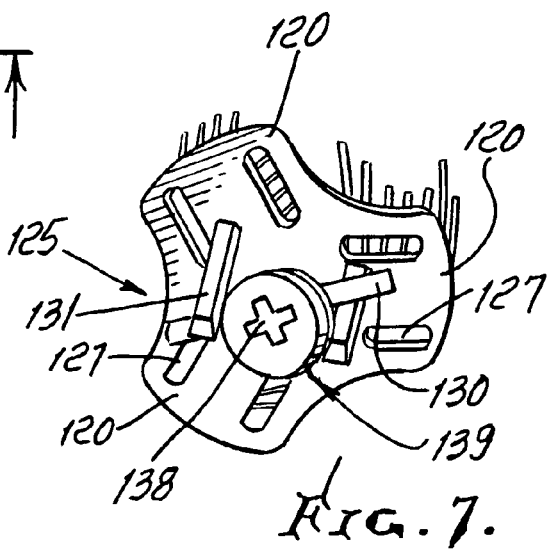
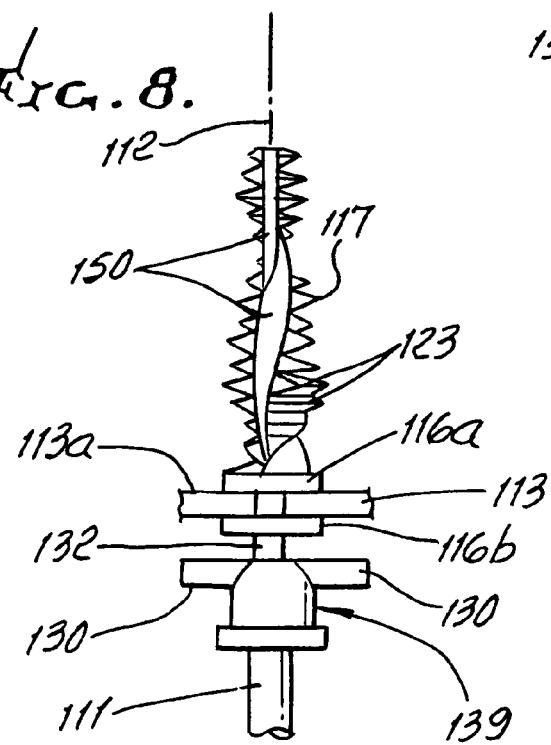

ROTARY DEVICE TO GATHER MUCOUS FOR TESTING

This application is a continuation-in-part of pending U.S. patent application Ser. No. 11/436,853, filed May 19, 2006.

BACKGROUND OF THE INVENTION

This invention relates generally to cervical cytology examinations, and more particularly to improvements in apparatus for conducting such examinations.

Cervical cytology examination has well been established as the procedure for the screening of cervical cancer and its precursors since the 1940s. Despite its long history, the procedure for the collection of cervical mucous (with the cervical cells) is far from perfect. Inadequacy rates reported by a study from the UK ranged from 0.2-35.5% (BMJ 1996). Much of the problem has been attributed to failure of collection or sampling devices. The methods as well as devices for the collection of the cervical cells described in this study have remained the same, even though the report was published 10 years ago. There is need for an improved system for the collection of cervical mucous that markedly increases the yield of endo- as well as ecto-cervical cells, for Pap smear cytology examination.

SUMMARY OF THE INVENTION

It is a major object of the invention to provide improvements in mucous gathering, as referred to above. Basically, the improved cervical mucous gathering device comprises:
 a) an elongated rotatable stem having a longitudinal axis,
 b) a headpiece carried at an end of the stem for angular flexing as the stem and headpiece rotate,
 c) the headpiece having a face sized for presentation to the cervix entrance as the headpiece rotates about an axis angled relative to the stem,
 d) said face having associated flexible means for gathering and retaining mucous proximate the cervix as the head rotates,
 e) and a flexible rotary probe carried by the headpiece, said probe projecting beyond said associated means and defining edges spaced apart spirally to propel mucous toward the headpiece in response to probe rotation.

Additional objects include provision of:
1. A flexible headpiece to facilitate more complete contact with the surface of the cervix. Anatomically, the axis of the cervix does not always align with the axis of the vagina. This is due to the mobile positions of the uterus and therefore the cervix. Any uterine tilting changes the plane of the surface of the cervix from a perpendicular position relative to the axis of the vagina. A rigid, flat conventional device makes no allowance for such common anatomical variation, resulting in the incomplete sweeping of the cervical surface. On the contrary, the flexible means such as curved bristles on the flexible headpiece as disclosed herein ensure maximum pick-up and retention as by capillary action of the mucous (and cervical cells) during the rotary scraping motion. The bristles of the device literally "hug" the cervix throughout the collection process to eliminate non-contact or skip areas. This is especially so when the surface contour is rough and irregular due to physiological or pathological variations. Skip areas account for part of the inadequacy rate of the Pap smear process. The present flexible headpiece and bristles are much less traumatic to the cervix as well.

2. The disc or shield type of headpiece as disclosed further ensures more complete contact. This is in opposition to prior devices, use of which often result in skip areas during rotation. The disc shape allows an even application for a smooth rotary action. Fenestrations on or in the disc plate increase the retention of mucous by the disc itself as by physical capillary action. This headpiece may be detachable for use with liquid preparation methods.

3. The flexible rotary probe enters the cervix, gathers mucous and propels or displaces such mucous toward the headpiece, for retention, in response to rotation of the probe.

4. The headpiece on the disc plate is preferably 3-flanged and star-shaped and bristles are in three groups, on the flanges, and conform to the cervix contour, to allow an even and more complete sweep of the cervix surface—a distinct improvement over conventional flat/brush devices. The bristle ends are typically shaped to allow efficient contact of both endo- and ecto-cervial parts of the cervix, as the device is rotated.

5. The stem piece of the device may be sheathed to allow a smooth rotary action. With one hand of the operator holding the sheath, and at the same time, applying the right amount of gentle pressure against the cervix via the stem for snug and firm contact, the user's other hand may rotate the stem, for example for 1½-2 complete turns, to collect the mucous, the axis of the rotating headpiece flexing relative to the axis of the stem, to efficiently follow cervix contour. This two-handed procedure has many advantages as compared to the conventional single-handed method of use.

A further object is to provide a method of using the said device, which includes the steps
 i) manually manipulating the device to bring the headpiece face into presentation to the cervix,
 ii) manually manipulating the device to rotate the stem, headpiece, and probe while holding the sleeve against rotation, thereby to gather mucous on said face, and transfer mucous toward that face.

Additional steps may include:
 iii) allowing the stem to flex during said step ii),
 iv) initially providing edges on and outstanding from said headpiece and flanges to gather mucous as the bristles and probe edges are rotated to maintain contact with the cervix,
 v) forming the bristles to have curved ends that brush against the cervix, with wiping action,
 vi) providing a rotary headpiece to support the probe and edges, and manipulating the sleeve to detach the headpiece from the stem following said step ii).

These and other objects and advantages of the invention, as well as the details of an illustrative embodiment, will be more fully understood from the following specification and drawings, in which:

DRAWING DESCRIPTION

FIG. 3 is a side elevation of a probe also seen in FIG. 1;

FIG. 4 is a schematic view showing bristle curvature;

FIG. 5 shows the headpiece being rotated by the stem as the headpiece is angled relative to the stem;

FIG. 6 is a side view of a modified headpiece;

FIG. 7 is an end view taken on lines 7-7 of FIG. 6, and tilted; and

FIG. 8 is a side elevation view of a probe employed with the FIG. 6 headpiece.

DETAILED DESCRIPTION

Figure 1:
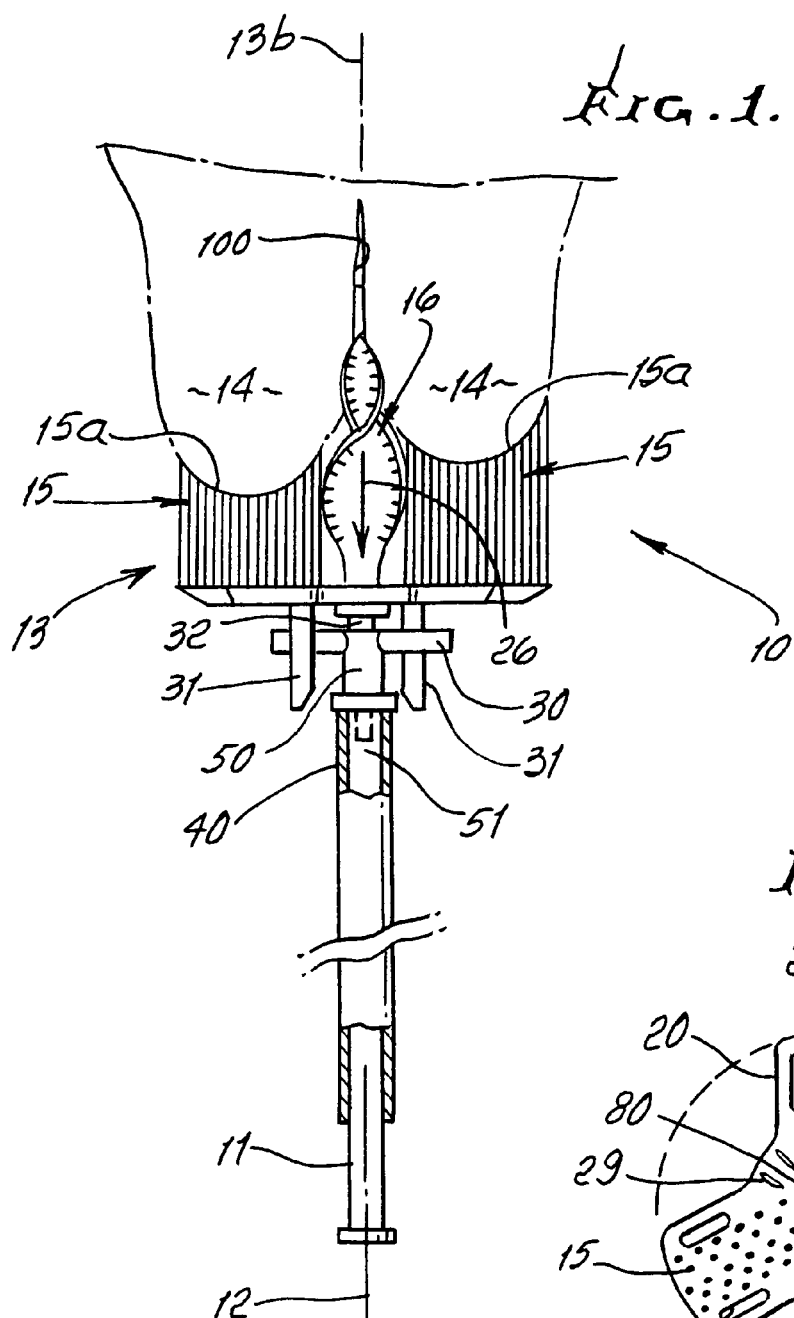
FIG. 1 is a side elevation showing a preferred form of the device.

In basic form, the mucous gathering device 10 comprises:
 a) an elongated manually rotatable stem 11 having a longitudinal axis 12;
 b) and a rotary headpiece 13 carried at a stem forward terminal end;
 c) the headpiece having a face 13a sized for forward presentation to the cervix 14, as the headpiece rotates, i.e. is rotated about its axis 13b at times when the stem is angled relative to the headpiece stem (see FIG. 5);
 d) the face 13a having associated flexible means, as for example soft bristles 15, projecting forwardly from the headpiece, for gathering mucous proximate the cervix, as the headpiece rotates;
 e) and a flexible rotary probe 16 carried as at 16a to project forwardly and centrally, typically beyond the bristles, the probe defining angled edges 17 spaced apart to gather and propel mucous rearwardly and generally toward the headpiece in response to probe rotation in an opening 100 defined by the cervix.

Figure 2:
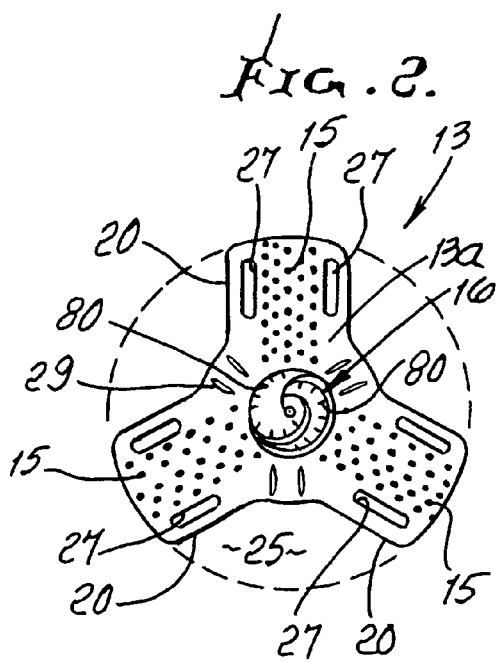
FIG. 2 is a top plan view of a headpiece.

FIGS. 1 and 2 show the bristles 15 projecting from three radially projecting headpiece flanges 20 spaced about the axis 13b, and together defining the face or faces 13a, the bristles terminals 15a defining U-shaped concave curvature corresponding to and to conform to the convex surface of the cervix, in axial radial planes, as the bristles sweep or scrape over its surface during rotation. Also, the bristle terminals 15a may be sidewardly angled, as shown at 15aa in FIG. 4, to aid mucous sweeping action.

The probe 16 is shown in FIG. 3 as having flute-like interrupted protrusions 23 defining the referenced edges 17 to extend in spiral configuration about and lengthwise of the axis 13b. The probe may consist of flexible plastic material, and the bristles also consist of said material.

The headpice flanges 13a define space 25 therebetween for mucous displacement in axial direction, indicated by arrows 26 in FIG. 1. The flanges may themselves define circularly spaced perforations 27 to pass gathered mucous in directions 26, as the headpiece rotates. Wide, blade shaped bristles 29 may be carried by the headpiece closer to the axis 13b, to aid in mucous gathering.

FIG. 1 also shows a rotary drive connection between the stem and headpiece. It includes radial projections 30 on the stem, and axial projections 31 on the headpiece which extend axially in interference relation to the projections 30, for loose coupling thereto as the stem rotates, and allowing angular flexing of the headpiece 13, as in FIG. 5. A narrow, central, flexible pivot connection between the stem and the central part of the headpiece is seen at 32. That pivot allows angular pivoting of the headpiece relative to the stem, and the loose rotary drive coupling of the projections 30 and 31 also accommodates such variable pivoting of the headpiece, as the bristles sweep over the cervix surface, to conform to angular misalignment of the cervix and vaginal axes, mucous gathering being uninterrupted.

A loose fitting sleeve 40 extends about the stem, and allows two handed manipulation, i.e. the sleeve may be grasped by the physician's left hand to angular orient the headpiece, while the stem is grasped by the right hand to rotate the stem and headpiece. An axial push-on, push-off connection of the stem part 50 closest to the headpiece relative to the stem part 51 closest to the sleeve, allows ready disconnection of the headpiece off the sleeve, for collection of mucous off the headpiece for a PAP test.

Hair-like bristles 80 on the headpiece, spaced about and close to axis 13b, act to retain gathered mucous, by capillary action.

The method of using the device includes
 i) manually manipulating said device to bring said face into presentation to the cervix,
 ii) manually manipulating the device to rotate the stem, headpiece, and probe while holding the sleeve against rotation, thereby to gather mucous on said face, and transfer mucous to said face,
 iii) and manually manipulating said device to retrieve said headpiece, and remaining gathered mucous.

Further steps include allowing the headpiece to flex relative to the stem, during said step ii); and manipulating the sleeve to detach the head from the stem following said step ii).

Referring to FIGS. 6-8, the modified apparatus includes certain elements corresponding to those in FIGS. 1-5, and bearing the same numerals prefaced by a "1".

Probe 116 is carried by or associated with the headpiece 113, as for example by headpiece base 113c extending between spaced flanges 116a and 116b on the probe, as seen in FIG. 8. Probe protrusions 123 extend only part way about axis 112 to define channels 150 for travel of mucous generally axially toward the base 113c.

Radial wing-like projections 130 are on the stem connector part 139, that axially interfits the stem as at grooves 138 in 139. Projections 130 interfit axial projections on the headpiece base, to rotatably drive the headpiece. Pivot connector 132 allows headpiece pivoting, as shown in FIG. 5, while maintaining loose coupling of 130 and 131.

I claim:
 1. A mucous gathering device, comprising:
 a) an elongated rotatable stem having a longitudinal axis,
 b) a rotary headpiece carried at an end of the stem for angular flexing as the stem rotates,
 c) the headpiece having a face sized for presentation to the cervix entrance as the headpiece rotates about an axis angled relative to the stem,
 d) said face having associated flexible means for gathering and retaining mucous proximate the cervix as the headpiece rotates,
 e) and a flexible rotary probe carried by the headpiece, said probe projecting forwardly and centrally relative to said associated flexible means and defining edges spaced apart to gather and propel mucous generally toward the headpiece in response to probe rotation in an opening defined by the cervix,
 f) and including first flexible drive elements operatively connected to the stem and projecting radially relative to the stem longitudinal axis, and second flexible drive elements operatively connected to the headpiece and projecting generally longitudinally relative to the stem and everywhere spaced from the stem, there being a universal pivot for the headpiece, the pivot spaced from all said elements, said first drive elements having free first terminals and said second drive elements having free second terminals, said free first terminals everywhere spaced from said free second terminals and spaced about said stem axis from the free second terminals, the second driven elements projecting in the paths of rotation of the first drive elements about said stem axis to become drivingly and flexibly interengaged with said first drive elements, all said elements projecting free of said universal pivot, g) said first and second drive elements, consisting of prongs, wherein each first drive element prong interengages a second drive element prong from a pair, wherein each pair of first and second prongs having cruciform interengagement.

2. The device of claim 1 including a sleeve extending about the stem to be manually manipulated as the stem rotates.

3. The combination of claim 1 wherein said associated flexible means includes flexible bristles having angled end portions disposed about an axis of rotation define by the face, for wiping mucous from the cavity in response to headpiece rotation.

4. The combination of claim 3 wherein the probe extends centrally of the headpiece, both sidewardly and forwardly of the bristles.

5. The combination of claim 4 wherein said bristles have terminals defining curvature in axial radial planes conforming to cervix curvature.

6. The combination of claim 3 said bristles spaced about and closed to said axis to retain mucous by capillary action.

7. The combination of claim 6 wherein said bristles are arranged in three groups about said axis.

8. The combination of claim 1 including openings in the headpiece, at its face, to gather and retain mucous, as the headpiece is rotated.

9. The combination of claim 1 wherein the headpiece has releasable connection to the stem.

10. The method of using the device of claim 2, which includes
  i) manually manipulating said device to bring said face into presentation to the cervix,
  ii) manually manipulating the device to rotate the stem, headpiece, and probe while holding the sleeve against rotation, thereby to gather mucous on said face, and transfer mucous to said face,
  iii) and manually manipulating said device to retrieve said headpiece, and remaining gathered mucous.

11. The method of claim 10 including allowing the headpiece to flex relative to the stem, during said step ii).

12. The method of claim 11 including manipulating the sleeve to detach the head from the stem following said step ii).

13. The apparatus of claim 1 wherein said pivot comprises a single flex connection at said axis.

* * * * *